United States Patent [19]

Kubota

[11] Patent Number: 6,051,219
[45] Date of Patent: Apr. 18, 2000

[54] METHOD FOR REDUCING MALODOR WITH *BACILLUS SUBTILIS* KUBOTA

[76] Inventor: Toyoaki Kubota, 2-27-19, Todoroki, Setagaya-ku, Tokyo, Japan

[21] Appl. No.: 08/913,045

[22] PCT Filed: Mar. 12, 1997

[86] PCT No.: PCT/JP97/00778

§ 371 Date: Sep. 5, 1997

§ 102(e) Date: Sep. 5, 1997

[87] PCT Pub. No.: WO97/33487

PCT Pub. Date: Sep. 18, 1997

[30] Foreign Application Priority Data

Mar. 14, 1996 [JP] Japan ........................... 8-84511

[51] Int. Cl.$^7$ .............................. A01N 63/00; C12N 1/20; C12Q 1/02
[52] U.S. Cl. .................. 424/93.462; 435/252.5; 435/839; 435/29; 435/264
[58] Field of Search ................ 424/93.462; 435/252.5, 435/29, 264, 839

[56] References Cited

U.S. PATENT DOCUMENTS 4,996,055  2/1991  Kurasawa ................. 424/442
5,540,924  7/1996  Onishi et al. ............. 424/93.4
5,549,890  8/1996  Kubo ..................... 424/93.462

FOREIGN PATENT DOCUMENTS

| | | |
|---|---|---|
| 2154590 | 12/1977 | Japan . |
| 5143916 | 11/1980 | Japan . |
| 1-144971 | 6/1989 | Japan . |
| 1-293195 | 11/1989 | Japan . |
| 4-05336895 | 12/1993 | Japan . |
| 7-241169 | 9/1995 | Japan . |
| 7-258049 | 9/1995 | Japan . |
| 9733487 | 9/1997 | WIPO . |

*Primary Examiner*—Irene Marx
*Assistant Examiner*—Vera Afremova
*Attorney, Agent, or Firm*—Browdy and Neimark

[57] ABSTRACT

The present invention relates to an oral composition containing *Bacillus subtilis* Kubota FERM BP-5847 for animals.

The oral administration of *Bacillus subtilis* Kubota FERM BP-5847 can deodorize feces and urine from livestock, poultry, fish and the like and also suppresses the occurrence of diarrhea.

8 Claims, No Drawings

METHOD FOR REDUCING MALODOR WITH *BACILLUS SUBTILIS* KUBOTA

FIELD OF THE INVENTION

The present invention relates to an oral composition for animals; more specifically, the present invention relates to an oral composition containing *Bacillus subtilis* Kubota for animals.

PRIOR ART

A vast amount of feces and urine is discharged from pigs, poultry and other livestock during feeding in pig-pens, poultry farms and various livestock houses, from which a very strong unpleasant odor evolves, causing a serious pollution problem.

A bad odor from feces and urine is generated not only from livestock farmers but also from pets in individual homes and animals and fish and shellfish in zoos and aquariums. Therefore, there is a need to deodorize the odor.

PROBLEM TO BE SOLVED BY THE INVENTION

Taking into account such demands from the industry, it is an object of the present invention to develop a new system capable of deodorizing a wide variety of excreta from not only livestock but also from pets and other animals and birds, efficiently in a simple fashion.

SUMMARY OF THE INVENTION

The present inventor has made investigations from various angles so as to attain the object. Focusing attention on the current status of using microorganisms such as yeast, vibrio and activated sludge as the bacteria for treating sewage, the present inventor has further screened useful bacterial strains as scum treating bacteria and deodorizing bacteria. Then, the inventor has successfully separated a bacterial strain from soil, which can reduce scum when used as a sewage treating bacterium and has a remarkable deodorizing effect.

It is confirmed that the bacterial strain thus separated bacteriologically belongs to *Bacillus subtilis*, but the useful properties thereof such as scum reduction and deodorizing action cannot be observed in conventional *Bacillus subtilis* strains. Therefore, the separated strain has been regarded as a new bacterial strain of *Bacillus subtilis* and named *Bacillus subtilis* Kubota.

The bacterial strain has been deposited under *Bacillus subtilis* Kubota FERM BP-5847 in the National Institute of Bioscience and Human-Technology, Agency of Industrial Science and Technology, Japan. This deposit is the deposit transferred on Mar. 3, 1997 from the National deposit No. FERM P-9643 deposited in Oct. 8, 1987.

*Bacillus subtilis* Kubota (sometimes referred to as "the bacterial strain" or "BSK bacterium" hereinbelow) directly sprayed on feces and urine can efficiently deodorize feces and urine. An extremely useful novel finding has been obtained unexpectedly that when the bacterial strain is administered orally, feces and urine with no bad odor are excreted.

Accordingly, the inventor has found not only direct deodorizing effect of the BSK bacterium to deodorize feces and urine if the bacterium is applied directly to feces and urine but also so-called indirect deodorizing effect of the BSK bacterium to deodorize feces and urine when the bacterium is orally administered, and have continued further investigations. Thus, the present invention has been attained.

In other words, the present invention is essentially based on the technical concept of an oral composition containing *Bacillus subtilis* Kubota for animals.

The present invention will now be described below in detail.

DETAILED DESCRIPTION OF THE INVENTION

In the present invention, *Bacillus subtilis* Kubota (BSK bacterium; FERM BP-5847) is used as the deodorizing micro-organism. As has been described above, the BSK bacterium is regarded bacteriologically to belong to *Bacillus subtilis*, but characteristically the bacterium has an excellent usefulness such as deodorizing action.

The bacteriological properties are described below.
(a) Morphology
1. Shape and size of the cell
    Short and small bacillus (1.2–1.4×3.6–3.8 $\mu$m).
2. Cellular Polymorphism
    No specific polymorphism. Being surrounded with cell membrane and having a nucleus. Also having spore, characteristically, with septum observed.
3. Presence or Absence of Mobility
    Mobile. About ten flagella.
4. Presence or Absence of Spore
    Spore present.
5. Gram Staining
    Gram positive. Stained blue with FAVOR-GSET (Nissui Pharmaceutical Co. Ltd.).
6. Acid-fast Property
    Stained red with Ziehl-Neelsen staining.
    Acid-fast bacterium.
(b) Growth State in Individual Culture Media
    Inoculating the bacterium suspender in a physiological saline onto a meat broth agar plate, for cultivation at 37° C. for 24 hours, a good growth is obserbed.
    The periphery of the cology is of R-type, not a round shape. The color is opaque and pale yellow.
    During sheep blood agar cultivation, heart infusion agar cultivation and TRYPTO-SOYA-AGAR cultivation, the colonies are of R-type, opaque and pale yellow with good growth. The growth state in each of the culture media is as follows;
    plain agar medium : (+)
    sheep blood agar medium : (+)
    heart infusion : (+)
    TRYPTO-SOYA (Nissui Pharmaceutical Co. Ltd.) : (+)
    Sabouraud : (−)
    salt egg agar medium : (−)
    Drigalski : (−)
    Brain-heart infusion liquid medium: (+).
(c) Physiological Properties
    (1) Reduction of nitrate : (+)
    (2) VP test (+)
    (3) Indole generation : (−)
    (4) Hydrogen sulfide generation : (−)
    (5) Starch hydrolysis (+)
    (6) Citric acid utilization : (+)
    (7) Dye generation : water soluble
    (8) Urease : (−)

(9) Oxidase (+)
(10) Catalase (+)

| (11) | Growth | acid | poor |
|------|--------|------|------|
|      |        | neutral | good |
|      | Temperature | 37° C. | good |
|      |        | 30° C. | good |
|      |        | 25° C. | good |
| (15) | Performance in oxygen | | aerobic |
| (16) | O–F test | | F |

(17) Generation of acid and gas from sugars

|  | acid | gas |
|---|---|---|
| L-arabinose | (−) | (−) |
| D-xylose | (−) | (−) |
| D-glucose | (+) | (−) |
| D-fructose | (+) | (−) |
| maltose | (+) | (−) |
| sucrose | (−) | (−) |
| lactic acid | (−) | (−) |
| trehalose | (±) | (−) |
| D-sorbitol | (−) | (−) |
| D-mannitol | (−) | (−) |
| D-inositol | (−) | (−) |
| starch | (−) | (−) |
| (d) Other properties | | |
| Esculin decomposition | | (+) |
| Cellulose decomposition | | (+) |
| Malonic acid utilization | | (+) |
| Arginine decomposition | | (−) |
| Lysine decarboxylation | | (+) |
| Ornithine decarboxylation | | (−) |
| Phenylalanine deamination | | (−) |
| Hemolytic property | | β-type hemolysis |
| Auxotrophy | | (+) |
| β-galactosidase | | (−) |

The novel strain *Bacillus subtilis* Kubota isolated in the present invention exhibits good growth in any common nutrient medium. Extract solutions from poultry feces, extract solutions from livestock feces, etc. particularly serve as an excellent culture broth.

In cultivation at 20 to 40° C., preferably 30 to 38° C. for 10 to 24 hours with or without using an incubator, the strain shows an excellent growth.

The resulting culture may be used as it is, because the culture contains a great amount of the cells thereof.

Additionally, the cells may be separated by centrifugation or the like from the culture, which are then thoroughly washed and used as they are as the cultivated cells; such cells may be used as a paste form such as wet cake in the above case or the cells may be further freeze-dried; alternatively, the cells may be diluted and prepared in suspension, for use in the form of such a processed product. It is needless to say that the processed product of the culture may also be used similarly. BSK bacterium (including the culture and the processed products thereof) of themselves may be used in the form of oral composition; additionally, the cells may be formulated into pharmaceutical agents for animals, after addition and mixing of starch, talc and other routine components into the cells. As the formulation, powder, granule, table, liquid, paste and other forms may appropriately be selected.

The oral composition in accordance with the present invention may be formulated as feed type, and in such a case, the cells of BSK bacterium may, of course, be added as they are into feeds; besides, the cells may be prepared preliminarily as a premix, which may be used; or the cells formulated as the aforementioned pharmaceutical type may De added into feeds.

Namely, the oral compostion of the present invention may be used as a pharmaceutical type or a feed type; and the cells of BSK bacterium (after premixed or formulated if necessary) may directly be administered orally as they are or they may be added and mixed as a feed additive into feeds or drinking water prior to intake. For drinking water, the cells of BSK bacterium may be directly added and mixed into drinking water and additionally, the cells of BSK bacterium may be packaged in a water-permeable bag which may be hung in a tank of drinking water. Furthermore, the cells of BSK bacterium may be possibly mixed with a feed or a pet food product or a drink product, for preparation as a final feed product. The amount of the microorganism in a feed varies depending on the species, age, etc. of a subject animal, but it may satisfactorily be said as a tentative standard that the BSK bacteria added in feeding water should be fed ad libtum at $10^7$ cells per pig weighing 70 kg per day.

At oral administration tests in mice, the $LD_{50}$ of BSK bacterium to be used in the oral composition of the present invention is nearly infinite; at coating tests on murine skin, no change has been observed. Hence, no problem in safety is noticed. Therefore, BSK bacterium can be used safely, without any adverse effect on animals at other microbial doses above the dose described previously.

Still furthermore, BSK bacterium has already been tested for safety at the TOKYO FOOD SANITATION ASSOCIATION, FOOD RESEARCH LABORATORY, which is an inspection organization authorized by the Minister of Health and Welfare. In that respect, the safety of the bacterium has been validated.

As has been described above, the composition of the present invention has prominent characteristics in that the composition orally administered can deodorize feces indirectly in a sense, in addition to direct application thereof over feces and urine.

Therefore, the use of the composition simply added into assorted seeds, other feeds or drinking water and the like, or simple feeding of the composition as a feed, pet food, liquid, etc. can deodorize feces and urine. Thus, laborious works can be skipped with the resultant energy saving; labor can be saved an environment with bad odor in particular, which is advantageous for not only workers for cattle farmers but also near-by residents of such cattle farmers because they can be free from the bad odor. Thus, the present invention is very excellent in terms of pollution control.

According to the present invention, furthermore, feces and urine from pets in homes and pet shops, animals at zoos and aquariums, and animals at pet hotels and veterinary clinics can be deodorized in a simple manner, so bad odor therefrom can be eliminated from these environment; even if feces and urine are left to stand alone, the generation of bad odor can be suppressed. In light of this point, the present invention is prominent.

Still further, the composition of the present invention, if put as it is or together with feeds in a water tank or a fish preserve, can prevent the generation of bad odor in the water therein. Therefore, the present invention is very useful in cleaning up water at aquariums, fish preserves and fishing ponds, and water in water tanks for tropical fish and other pets at homes and pet shops, and in preventing the generation of bad odor or fishy odor.

Furthermore, the composition of the present invention has a good action of curing intestinal disorder, and when administered orally, the composition distinctively suppresses the occurrence of diarrhea. Particularly, pigs are animals readily having loose bowels, so if the occurrence of diarrhea is suppressed in young pigs, they can make good growth, leading to the increase of profit. Additionally, chicken and other animals can dramatically elevate the projection of meat and eggs. From these respects, the present invention is very excellent.

Examples of the present invention will now be described hereinbelow.

EXAMPLE 1

| Starch | 10 g |
|---|---|
| Meat extract | 3 g |
| Peptone | 10 g |
| Sodium chloride | 5 g |
| Water | 1,000 ml (pH 7.0) |

The medium of the composition described above was placed in a 500-ml flask, into which was inoculated *Bacillus subtilis* Kubota FERM BP-5847, for stationary culture at 37° C. for 20 hours.

The resulting culture broth was centrifuged to recover the cells, which were then mixed with 300 g of starch. The resulting mixture was defined as a microbial formulation.

EXAMPLE 2

Commercially available growing feeds were fed to 50 young pigs at the stage of growth maintained at a pig farmer. The cells of BSK strain recovered in Example 1 were added to drinking water to $10^5$ cells/day, and the resulting water was fed ad libitum.

One month later, the odor and ammonia concentration in the pig-pens were determined. The concentration of the odor was determined by the three-point comparison method (Notification No. 238 of the Metropolitan Environmental Pollution Control Ordinate), while the ammonia concentration was measured by an ammonia detector.

Consequently, the concentration of the odor, which was 117 prior to feeding, was reduced to 74 after feeding (one month later), which means odor reduction and elimination by as much as by 37%. Alternatively, the ammonia concentration was 2.3 prior to feeding but 1.0 after feeding (one month later), which means the ammonia was reduced and eliminated by as much as 57%. During the growing term, eight of the young pigs had diarrhea, but one month later, then, no young pig with diarrhea was observed.

EXAMPLE 3

Twenty dairy cows were divided in two groups, of ten cows, each and then, green oats as a crude feed was blended with a commercially available feed. Subsequently, the resulting feed was further blended with the microbial formulation as prepared in Example 1; the added amount of the microbial formulation was 0.1%. The resulting mixture was fed to a test lot of 10 dairy cows for one week. On contrast, the feed with no addition of the microbial formulation was fed to a control lot of 10 dairy cows.

One week later, no specific bad odor was observed in the dairy cow houses of the test lot, and even in the dairy cow houses wherein feces and urine were left to stand as they were, milking was performed with no disturbance. In contrast, unendurable smell filled in the diary cow houses of the control lot throughout a term of one week. Even in the test lot, however, the cessation of the microbial feeding caused generation of a bad smell on the very next day.

EXAMPLE 4

A feed was prepared by adding the freeze-dried product containing starch of the cells as prepared in Example 1 at 0.2% into a commercially available goldfish feed, and the feed was used to feed goldfish in a commercially available round goldfish basin.

Despite no change of water or no cleaning of the goldfish basin for a month, the water in the goldfish basin was clean, with no occurrence of a bad odor such as a fishy odor.

Effect of the Invention

A bad odor from a variety of animals including fish can be eliminated by the oral administration of BSK bacterium and therefore, the composition of the present invention can be applied widely not only to fish, cattle and poultry in homes and of cattle farmers and fish breeders but also to pets, experimental animals and animals at zoos and aquariums. Hence, the composition serves very well for pollution control of a bad odor currently drawing serious concern, which enables the establishment of a livestock industry in the suburbs of cities and also serves markedly for livestock farmers in the suburbs of cities. Thus, the composition contributes much for the propagation of the domestic livestock industry.

Reference to the Microorganism Deposited under the Provision of Article 13-2

1. *Bacillus subtilis* Kubota
   a. Name and address of the depository at which the microorganism was deposited;
   name: The National Institute of Bioscience and Human-Technology, Agency of Industrial Science and Technology, Ministry of International Trade and Industry
   address: 1–3, Higashi 1 chome, Tsukuba-shi, Ibaraki-ken, 305, Japan
   b. Deposition date at the depository (a) Oct. 8, 1987
   c. Accession Number of the deposition, designated by the depository (a) FERM BP-5847

I claim:

1. A method for reducing the malodor in feces and urine consisting essentially of orally administering to livestock an amount effective of a member selected from the group consisting of cells of *Bacillus subtilis* Kubota, FERM BP-5847; a culture of *Bacillus subtilis* Kubota, FERM BP-5847; freeze-dried cells of *Bacillus subtilis* Kubota, FERM BP-5847; and freeze-dried culture of *Bacillus subtilis* Kubota, FERM BP-5847, which results in a decrease in the malodor of the feces and urine produced by said livestock.

2. The method according to claim 1, wherein the member is administered in a feed composition.

3. The method according to claim 1, wherein the member is administered in drinking water.

4. The method according to claim 1, wherein the member is administered in a feed composition containing freeze-dried cells of *Bacillus subtilis* Kubota, FERM BP-5847.

5. The method according to claim 1 wherein the member is freeze-dried.

6. The method according to claim 1 wherein the member is diluted and prepared in a suspension.

7. The method according to claim 1 wherein the member is mixed with a carrier.

8. The method according to claim 1 wherein the carrier is starch.

* * * * *